United States Patent
Bojarski et al.

(10) Patent No.: US 10,253,165 B2
(45) Date of Patent: Apr. 9, 2019

(54) CONTROL OF ORGANIC IMPURITIES IN POLYCARBONATE SYNTHESIS

(71) Applicant: SABIC Global Technologies B.V., Bergen op Zoom (NL)

(72) Inventors: Aaron David Bojarski, Murcia (ES); Jorge A. Garcia Agudo, Murcia (ES)

(73) Assignee: SABIC Global Technologies B.V., Bergen op Zoom (NL)

( * ) Notice: Subject to any disclaimer, the term of this patent is extended or adjusted under 35 U.S.C. 154(b) by 0 days.

(21) Appl. No.: 15/553,279

(22) PCT Filed: Feb. 25, 2016

(86) PCT No.: PCT/IB2016/051041
§ 371 (c)(1),
(2) Date: Aug. 24, 2017

(87) PCT Pub. No.: WO2016/135672
PCT Pub. Date: Sep. 1, 2016

(65) Prior Publication Data
US 2018/0208746 A1    Jul. 26, 2018

(30) Foreign Application Priority Data
Feb. 26, 2015 (EP) .................................... 15382083

(51) Int. Cl.
*C08G 63/02* (2006.01)
*C08K 5/50* (2006.01)
*C08G 64/20* (2006.01)
*C08G 64/30* (2006.01)
*C08G 64/42* (2006.01)
*C08L 69/00* (2006.01)
*G06F 19/00* (2018.01)

(52) U.S. Cl.
CPC ................ *C08K 5/50* (2013.01); *C08G 64/20* (2013.01); *C08G 64/307* (2013.01); *C08G 64/42* (2013.01); *C08L 69/00* (2013.01); *G06F 19/702* (2013.01)

(58) Field of Classification Search
USPC .................................................. 528/196, 198
See application file for complete search history.

(56) References Cited

U.S. PATENT DOCUMENTS

| | | |
|---|---|---|
| 6,583,258 B1 | 6/2003 | Lemmon et al. |
| 6,956,072 B1 | 10/2005 | Kanaka et al. |
| 8,962,788 B2 | 2/2015 | Fernandez et al. |
| 9,732,028 B2 | 8/2017 | Fernandez et al. |
| 2003/0149223 A1 | 8/2003 | McCloskey et al. |

FOREIGN PATENT DOCUMENTS

| | | |
|---|---|---|
| EP | 0908484 A1 | 4/1999 |
| EP | 0943409 A1 | 9/1999 |
| EP | 2692767 A1 | 2/2014 |
| EP | 2937372 A1 | 10/2015 |
| WO | 0047679 | 8/2000 |
| WO | 2003014188 A1 | 2/2003 |

OTHER PUBLICATIONS

International Search Report for International Application No. PCT/IB2016/051041; International Filing Date: Feb. 25, 2016; dated Apr. 22, 2016; 5 Pages.

Written Opinion of the International Searching Authority for International Application No. PCT/IB2016/051041; International Filing Date: Feb. 25, 2016; dated Apr. 22, 2016; 8 Pages.

*Primary Examiner* — Terressa Boykin
(74) *Attorney, Agent, or Firm* — Cantor Colburn LLP (57) ABSTRACT

Polymerization processes comprising melt polymerizing a carbonate and a dihydroxy compound in the presence of an amount of a beta organic catalyst so as to give rise to a polycarbonate product, wherein the amount of beta organic catalyst comprises at least one onium salt and also comprises triphenyl phosphonium oxide (TPPO), and wherein the TPPO represents less than about 0.3 weight % of the sum of the weights of the at least one onium salt and the TPPO in the amount of beta organic catalyst.

20 Claims, 3 Drawing Sheets

CONTROL OF ORGANIC IMPURITIES IN POLYCARBONATE SYNTHESIS

CROSS-REFERENCE TO RELATED APPLICATIONS

This application is the National Stage of International Application No. PCT/IB2016/051041, filed Feb. 25, 2016, which claims the benefit of U.S. Provisional Application No. 15382083.2, filed Feb. 26, 2015, the disclosures of which are incorporated herein by reference in their entireties.

TECHNICAL FIELD

The present disclosure relates to polymerization catalysts.

BACKGROUND

The melt polycarbonate process is based on continuous reaction of a dihydroxy compound and a carbonate source in a molten stage. The reaction can occur in a series of reactors where the combined effect of catalyst, temperature, vacuum, and agitation allows for monomer reaction and removal of reaction by-products to displace the reaction equilibrium and effect polymer chain growth.

One common polycarbonate made in melt polymerization reactions is derived from bisphenol A (BPA) via reaction with diphenyl carbonate (DPC). This reaction can be catalyzed by, for example, tetra methyl ammonium hydroxide (TMAOH) or tetrabutyl phosphonium acetate (TBPA), which can be added in to a monomer mixture prior to being introduced to a first polymerization unit and sodium hydroxide (NaOH), which can be added to a reactor or upstream of a reactor and after a monomer mixer.

Apart from the main polymerization reaction, there is a series of side reactions consisting of chain rearrangements of the polymer backbone that lead to branching that are often referred to as Fries rearrangement. The Fries species specifically found in bisphenol A melt polycarbonates are the ester type of structures A, B, and C.

Linear Fries (A):

Branched Fries (B):

Acid Fries (C):

The Fries reaction is induced by the combined effect of basic catalysts, temperature, and residence time, which may make melt-produced polycarbonates inherently branched as compared with the interfacial polycarbonates, as their manufacturing temperatures are lower. Because high branching levels in the resin can have a negative effect on the mechanical properties of the polycarbonate (for example, on impact strength), a polycondensation catalyst with improved selectivity (i.e., reduced Fries promotion) is needed.

Production of polycarbonate by the melt method may also require use of two different catalysts, one of organic nature known as the beta catalyst, usually a onium salt (e.g., an hydrocarbon onium salt, such as an alkylphosphonium salt); the other catalyst (known as alpha catalyst) of inorganic nature, e.g., an alkali metal salt.

Because dual catalyst systems can at times present certain challenges to their users, there is a need in the art for improved such systems.

SUMMARY

In one aspect, the present disclosure provides polymerization processes. A process according to the present disclosure comprises: melt polymerizing a carbonate and a dihydroxy compound in the presence of an amount of a beta organic catalyst so as to give rise to a polycarbonate product, wherein the amount of beta organic catalyst comprises at least one onium salt and also comprises triphenyl phosphonium oxide (TPPO), and wherein the TPPO represents less than about 0.3 weight % of the sum of the weights of the at least one onium salt and the TPPO in the amount of beta organic catalyst.

The present disclosure also provides additional polymerization processes. Such a process comprises: (a) melt polymerizing in a first stage a carbonate and a dihydroxy compound in the presence of an amount of a beta organic catalyst so as to give rise to a polycarbonate oligomer product, wherein the amount of beta organic catalyst comprises at least one onium salt and also comprises triphenyl phosphonium oxide (TPPO), wherein the TPPO represents less than about 0.3 weight % of the sum of the weights of the at least one onium salt and the TPPO in the amount of beta organic catalyst, and wherein the polycarbonate oligomer product has an average molecular weight of less than or equal to about 13 kDalton (polystyrene basis) and exhibiting a Fries rearrangement level of less than, e.g., about 500 ppm; (b) reacting in a second stage the polycarbonate oligomer product and optionally a carbonate and a dihydroxy compound in the presence of an amount of a beta organic catalyst so as to give rise to a polycarbonate polymerized product, wherein the amount of beta organic catalyst comprises at least one onium salt and triphenyl phosphonium oxide (TPPO), and wherein the TPPO represents less than about 0.3 weight % of the sum of the weights of the at least one onium salt and the TPPO in the amount of beta organic catalyst, and wherein the polycarbonate polymerized product has an average molecular weight of more than about 13 kDalton (polystyrene basis) and wherein the polymerization product exhibits a Fries rearrangement level of from about 100 ppm to about 1200 ppm. Dalton and kDalton values presented herein are on a polystyrene basis.

The present disclosure also provides systems, the systems comprising: a reactor chain configured to synthesize a polycarbonate product; and an amount of beta organic catalyst, wherein the amount of beta organic catalyst comprises at least one onium salt and also comprises triphenyl phosphonium oxide (TPPO), and wherein the TPPO represents less than about 0.3 weight % of the sum of the weights of the at least one onium salt and the TPPO in the amount of beta organic catalyst. (The term "reactor chain" refers to two or more reactors capable of being placed into fluid communication with one another, e.g., a series of two, three, four, or even more reactors. A reactor chain may include, for example, an oligomerization unit and one or more downstream units that synthesize final product from the product of the oligomerization unit.)

This disclosure provides additional systems, such systems comprising: a reactor chain configured to synthesize a polycarbonate product; an amount of a carbonate disposed within the reactor chain; an amount of a dihydroxy compound disposed within the reactor chain; and an amount of beta organic catalyst disposed within the reactor chain, wherein the amount of beta organic catalyst comprises at least one onium salt and also comprises triphenyl phosphonium oxide (TPPO), and wherein the TPPO represents less than about 0.3 weight % of the sum of the weights of the at least one onium salt and the TPPO in the amount of beta organic catalyst.

BRIEF DESCRIPTION OF THE DRAWINGS

The summary, as well as the following detailed description, is further understood when read in conjunction with the appended drawings. For the purpose of illustrating the technology, there are shown in the drawings exemplary and preferred embodiments of the invention; however, the disclosure is not limited to the specific methods, compositions, and devices disclosed. In addition, the drawings are not necessarily drawn to scale. In the drawings.

DETAILED DESCRIPTION

Melt polycarbonate polymerization may be catalyzed by the combination of an alpha catalyst (e.g., alkali or alkaline earth metal salts, such as NaOH or $NaKH_2PO_4$) and a beta catalyst (such as tetraphenyl phosphonium acetate). As mentioned elsewhere herein, apart from the main polymerization reaction there is also a series of side reactions, also referred to as Fries rearrangement, consisting of chain rearrangements products of the polymer backbone that lead to branching.

The applicants have discovered that the presence of alkali metal salts in a beta catalyst, e.g., a beta catalyst comprising tetraphenyl phosphonium acetate (TPPA), can increase the level of branching in the polycarbonate. One such branching reaction is the Fries rearrangement reaction, which reaction may intensify in the presence of alpha catalyst (alkali metal salt), temperature and residence time.

To reduce the level of branching/Fries during the production of polycarbonate, the present disclosure provides certain beta catalyst options. A non-limiting list of exemplary beta catalysts includes tetrabutyl phosphonium acetate (TBPA), tetraphenyl phosphonium acetate (TPPA), and tetraphenyl phosphonium phenolate (TPPP).

One consideration during evaluation of a new raw material (catalyst) is the overall composition of the catalyst, as small amounts of organic or inorganic species can change the performance of the raw material and affect the quality of the polycarbonate produced. In connection with this consideration, the applicants have identified the effect of organic species related with the production/purification process of TPPA in the performance of the catalyst with respect to polycarbonate branching (also described by the Fries level).

Without being bound to any particular theory, during the production of TPPA certain amounts of triphenyl phosphonium oxide (TPPO) may be produced. Alternatively, TPPO may also be part of the impurities present initially in the raw materials used for the TPPA production. Triphenyl phosphine (TPP) can also be present as a degradation product of TPPA. These molecules are shown below:

form metal complexes, which—again without being bound to any particular theory—may be an indication of TPPO's basicity.

| Acronym | TBPA | TPPA | TPPO | TPP |
|---|---|---|---|---|
| Name | Tetrabutyl phosphonium acetate | Tetraphenyl phosphonium acetate | Triphenyl phosphonium oxide | Triphenyl phosphine |
| Formula | | | | |

Also without being bound to any particular theory, triphenylphosphine (TPP) catalytic activity may be explained by the presence of an electron pair which could form ion pairs with the PC chain, rendering active phenolate species as follows:

In the case of TPPO, the electron pair on P atom is not present, but oxygen that has three electron pairs that could be offered to an electron acceptor (electrophile). This can If one considers TPPO's basicity, then a catalytic mechanism can be postulated using TPPO instead of TPP, which (without being bound to any theory) may explain certain results.

If one considers the foregoing mechanisms, one might expect that the TPP catalytic effect is higher due to its higher basicity compared to the one observed for TPPO. Applicants determined that controlling the amount of TPPO can affect the degree of Fries rearrangement present during polycarbonate production. To that extent the amount of TPPO is suitably at most 0.3 weight %. Preferably the amount of TPPO is from 0.1 to 0.3, more preferably from 0.1 to 0.2, even more preferably from 0.1 to 0.15 weight % of the sum of the weights of the at least one onium salt and the TPPO in the amount of beta organic catalyst.

"Polycarbonate" as used herein means a polymer having repeating structural carbonate units of formula (1)

(1)

in which at least 60 percent of the total number of $R^1$ groups contain aromatic moieties and the balance thereof are aliphatic, alicyclic, or aromatic. Each $R^1$ can be a $C_{6-30}$ aromatic group, that is, contains at least one aromatic moiety. $R^1$ can be derived from an aromatic dihydroxy compound of the formula HO—$R^1$—OH, in particular of formula (2)

$$HO-A^1-Y^1-A^2-OH \qquad (2)$$

wherein each of $A^1$ and $A^2$ is a monocyclic divalent aromatic group and $Y^1$ is a single bond or a bridging group having one or more atoms that separate $A^1$ from $A^2$. One atom can separate $A^1$ from $A^2$. Specifically, each $R^1$ can be derived from a bisphenol of formula (3)

(3)

wherein $R^a$ and $R^b$ are each independently a halogen, $C_{1-12}$ alkoxy, or $C_{1-12}$ alkyl; and p and q are each independently integers of 0 to 4. It will be understood that when p or q is less than 4, the valence of each carbon of the ring is filled by hydrogen. Also in formula (3), $X^a$ is a bridging group connecting the two hydroxy-substituted aromatic groups, where the bridging group and the hydroxy substituent of each $C_6$ arylene group are disposed ortho, meta, or para (specifically para) to each other on the $C_6$ arylene group. The bridging group $X^a$ can be a single bond, —O—, —S—, —S(O)—, —S(O)$_2$—, —C(O)—, or a $C_{1-18}$ organic group. The $C_{1-18}$ organic bridging group can be cyclic or acyclic, aromatic or non-aromatic, and can further comprise heteroatoms such as halogens, oxygen, nitrogen, sulfur, silicon, or phosphorous. The $C_{1-18}$ organic group can be disposed such that the $C_6$ arylene groups connected thereto are each connected to a common alkylidene carbon or to different carbons of the $C_{1-18}$ organic bridging group. Each p and q can be 1, and $R^a$ and $R^b$ can each be a $C_{1-3}$ alkyl group, specifically methyl, disposed meta to the hydroxy group on each arylene group.

$X^a$ can be a substituted or unsubstituted $C_{3-18}$ cycloalkylidene, a $C_{1-25}$ alkylidene of formula —C($R^c$)($R^d$)— wherein $R^c$ and $R^d$ are each independently hydrogen, $C_{1-12}$ alkyl, $C_{1-12}$ cycloalkyl, $C_{7-12}$ arylalkyl, $C_{1-12}$ heteroalkyl, or cyclic $C_{7-12}$ heteroarylalkyl, or a group of the formula —C(=$R^e$)— wherein $R^e$ is a divalent $C_{1-12}$ hydrocarbon group. Groups of this type include methylene, cyclohexylmethylene, ethylidene, neopentylidene, and isopropylidene, as well as 2-[2.2.1]-bicycloheptylidene, cyclohexylidene, cyclopentylidene, cyclododecylidene, and adamantylidene.

$X^a$ can be a $C_{1-18}$ alkylene, a $C_{3-18}$ cycloalkylene, a fused $C_{6-18}$ cycloalkylene, or a group of the formula —$B^1$-G-$B^2$— wherein $B^1$ and $B^2$ are the same or different $C_{1-6}$ alkylene and G is a $C_{3-12}$ cycloalkylidene or a $C_{6-16}$ arylene. For example, $X^a$ can be a substituted $C_{3-18}$ cycloalkylidene of formula (4)

(4)

wherein $R^r$, $R^p$, $R^q$, and $R^t$ are each independently hydrogen, halogen, oxygen, or $C_{1-12}$ hydrocarbon groups; Q is a direct bond, a carbon, or a divalent oxygen, sulfur, or —N(Z)— where Z is hydrogen, halogen, hydroxy, $C_{1-12}$ alkyl, $C_{1-12}$ alkoxy, or $C_{1-12}$ acyl; r is 0 to 2, t is 1 or 2, q is 0 or 1, and k is 0 to 3, with the proviso that at least two of $R^r$, $R^p$, $R^q$, and $R^t$ taken together are a fused cycloaliphatic, aromatic, or heteroaromatic ring. It will be understood that where the fused ring is aromatic, the ring as shown in formula (4) will have an unsaturated carbon-carbon linkage where the ring is fused. When k is one and i is 0, the ring as shown in formula (4) contains 4 carbon atoms, when k is 2, the ring as shown in formula (4) contains 5 carbon atoms, and when k is 3, the ring contains 6 carbon atoms. Two adjacent groups (e.g., $R^q$ and $R^t$ taken together) can form an aromatic group, and $R^q$ and $R^t$ taken together can form one aromatic group and $R^r$ and $R^p$ taken together can form a second aromatic group. When $R^q$ and $R^t$ taken together form an aromatic group, $R^p$ can be a double-bonded oxygen atom, i.e., a ketone.

Bisphenols wherein $X^a$ is a cycloalkylidene of formula (4) can be used in the manufacture of polycarbonates containing phthalimidine carbonate units of formula (1a)

(1a)

wherein $R^a$, $R^b$, p, and q are as in formula (3), $R^3$ is each independently a $C_{1-6}$ alkyl, j is 0 to 4, and $R_4$ is hydrogen, $C_{1-6}$ alkyl, or a substituted or unsubstituted phenyl, for example a phenyl substituted with up to five $C_{1-6}$ alkyls. For example, the phthalimidine carbonate units are of formula (1b)

(1b)

wherein $R^5$ is hydrogen, phenyl optionally substituted with up to five 5 $C_{1-6}$ alkyls, or $C_{1-4}$ alkyl. In formula (1b), $R^5$ can be hydrogen, methyl, or phenyl, specifically phenyl. Carbonate units (1b) wherein $R^5$ is phenyl can be derived from 2-phenyl-3,3'-bis(4-hydroxy phenyl)phthalimidine (also known as 3,3-bis(4-hydroxyphenyl)-2-phenylisoindolin-1-one, or N-phenyl phenolphthalein bisphenol ("PPPBP")).

Other bisphenol carbonate repeating units of this type are the isatin carbonate units of formula (1c) and (1d)

(1c)

(1d)

wherein $R^a$ and $R^b$ are each independently $C_{1-12}$ alkyl, p and q are each independently 0 to 4, and $R^i$ is $C_{1-12}$ alkyl, phenyl, optionally substituted with 1 to 5 $C_{1-10}$ alkyl, or benzyl optionally substituted with 1 to 5 $C_{1-10}$ alkyl. Each $R^a$ and $R^b$ can be methyl, p and q can each independently be 0 or 1, and $R^i$ is $C_{1-4}$ alkyl or phenyl.

Other examples of bisphenol carbonate units derived from bisphenols (3) wherein $X^a$ is a substituted or unsubstituted $C_{3-18}$ cycloalkylidene (4) include the cyclohexylidene-bridged, alkyl-substituted bisphenol of formula (1e)

(1e)

wherein $R^a$ and $R^b$ are each independently $C_{1-12}$ alkyl, $R^g$ is $C_{1-12}$ alkyl, p and q are each independently 0 to 4, and t is 0 to 10. At least one of each of $R^a$ and $R^b$ can be disposed meta to the cyclohexylidene bridging group. Each $R^a$ and $R^b$ can independently be $C_{1-4}$ alkyl, $R^g$ is $C_{1-4}$ alkyl, p and q are each 0 or 1, and t is 0 to 5. $R^a$, $R^b$, and $R^g$ can each be methyl, p and q can each be 0 or 1, and t can be 0 or 3, specifically 0.

Examples of other bisphenol carbonate units derived from bisphenol (3) wherein $X^a$ is a substituted or unsubstituted $C_{3-18}$ cycloalkylidene include adamantyl units of formula (1f) and fluorenyl units of formula (1g)

(1f)

(1g)

wherein $R^a$ and $R^b$ are each independently $C_{1-12}$ alkyl, and p and q are each independently 1 to 4. At least one of each of $R^a$ and $R^b$ can be disposed meta to the cycloalkylidene bridging group. $R^a$ and $R^b$ can each be independently $C_{1-3}$ alkyl, and p and q can be each 0 or 1; specifically, $R^a$, $R^b$ can each be methyl, p and q are each 0 or 1, and when p and q are 1, the methyl group can be disposed meta to the cycloalkylidene bridging group. Carbonates containing units (1a) to (1g) are useful for making polycarbonates with high glass transition temperatures (Tg) and high heat distortion temperatures.

Other useful dihydroxy compounds of the formula HO—$R^1$—OH include aromatic dihydroxy compounds of formula (6)

(6)

wherein each $R^h$ is independently a halogen atom, $C_{1-10}$ hydrocarbyl group such as a $C_{1-10}$ alkyl, a halogen-substituted $C_{1-10}$ alkyl, a $C_{6-10}$ aryl, or a halogen-substituted $C_{6-10}$ aryl, and n is 0 to 4. The halogen is usually bromine.

Polycarbonate may be prepared via the melt polymerization of a bisphenol and a carbonate precursor (also referred to as a carbonate compound). In one embodiment, the carbonate precursor is a diaryl carbonate ester. In a further embodiment, the diaryl carbonate ester can be prepared by transesterification reaction containing a dialkylcarbonate, phosgenation of phenol, and other methods known to one of ordinary in the art, including, but not limited to, the use of one or more different types of catalysts The diaryl carbonate ester can be diphenyl carbonate, or an activated diphenyl carbonate having electron-withdrawing substituents on each aryl, such as bis(4-nitrophenyl) carbonate, bis(2-chlorophenyl)carbonate, bis(4-chlorophenyl)carbonate, bis(methyl salicyl)carbonate, bis(4-methylcarboxylphenyl) carbonate, bis(2-acetylphenyl) carboxylate, bis(4-acetylphenyl) carboxylate, or a combination comprising at least one of the foregoing.

In some embodiments, a user may use a purified diaryl carbonate. Such a purified diaryl carbonate may (but this is not a requirement) comprise less than or equal to 38 parts per billion by weight (ppb), specifically less than or equal to 23 ppb of molybdenum; less than or equal to 38 ppb, specifically less than or equal to 23 ppb vanadium; less than or equal to 38 ppb, specifically less than or equal to 23 ppb chromium; less than or equal to 85 ppb, specifically less than or equal to 57 ppb titanium; less than or equal to 425 ppb, specifically less than or equal to 284 ppb of niobium; less than or equal to 38 ppb, specifically less than or equal to 23 ppb of nickel; less than or equal to 12 ppb, specifically less than or equal to 6 ppb zirconium; less than or equal to 12 ppb, specifically less than or equal to 6 ppb of iron.

A polycarbonate according to the present disclosure (e.g., one made from the diaryl carbonate described above) may also (but this, again, is not a requirement) comprise less than or equal to 33 parts per billion by weight (ppb), specifically less than or equal to 20 ppb of molybdenum; less than or equal to 33 ppb, specifically less than or equal to 20 ppb vanadium; less than or equal to 33 ppb, specifically less than or equal to 20 ppb chromium; less than or equal to 75 ppb, specifically less than or equal to 50 ppb titanium; less than or equal to 375 ppb, specifically less than or equal to 250 ppb of niobium; less than or equal to 33 ppb, specifically less than or equal to 20 ppb of nickel; less than or equal to 10 ppb, specifically less than or equal to 5 ppb zirconium; less than or equal to 10 ppb, specifically less than or equal to 5 ppb of iron. Further details are found in European applications 13382087.8 and 13382085.2, both of which applications are incorporated herein by reference in their entireties for any and all purposes. Without being bound to any particular theory, the foregoing purity levels of the diaryl carbonate or the polycarbonate may influence the transparency, color, or both of the polycarbonate product.

In the melt polymerization process, the polycarbonate can be prepared by co-reacting, in a molten state, a dihydroxy reactant and a carbonate precursor in the presence of a transesterification catalyst. The reaction can be carried out in typical polymerization equipment, such as a continuously stirred reactor (CSTR), plug flow reactor, wire wetting fall polymerizers, free fall polymerizers, horizontal polymerizers, wiped film polymerizers, Banbury mixers, single or twin screw extruders, or a combination comprising one or more of the foregoing. Volatile monohydric phenol and other volatile components may be removed from the molten reactants by distillation and the polymer is isolated as a molten residue.

Melt polymerization can be conducted in a reactor chain as a batch process or as a continuous process. In either case, the melt polymerization conditions used can comprise two or more distinct reaction stages. For example, the polymerization can comprise a first reaction stage (also referred to as an oligomerization stage) in which the starting dihydroxy aromatic compound and diaryl carbonate are converted into an oligomeric polycarbonate and a second reaction stage (also referred to as a polymerization stage) wherein the oligomeric polycarbonate formed in the first reaction stage is converted to high molecular weight polycarbonate.

An oligomerization stage may comprise 1 or more, specifically, 2 or more, more specifically, 2 to 4 oligomerization units (for example 2 to 4 continuously stirred tanks). When 2 or more oligomerization units are present in series, one or both of an increase in temperature or a decrease in pressure can occur from one unit to the next.

The polymerization stage can comprise 1 or more, specifically, 2 or more, more specifically, 2 polymerization units (for example, 2 horizontal or wire wetting fall polymerizers). The polymerization stage can comprise a polymerization unit that can polymerize the polycarbonate to a molecular weight of, for example, about 20 to about 80 kDalton (polystyrene basis), after which the polycarbonate composition can then be optionally quenched, and introduced to a devolatization unit. In the devolatization unit, the molecular weight of the polycarbonate does not significantly increase (for example, the molecular weight does not increase by greater than 10 weight percent (wt %)) and a temperature, a pressure, and a residence time are used to reduce the concentration of low molecular weight components (e.g., those with a molecular weight of less than 1,000 Dalton on a polystyrene basis). The Fries level in a polymerization reactor may, in some cases, be around or even above 600 ppm for a comparatively high molecular weight of polycarbonate, e.g., 60 kDalton.

An oligomerization unit is herein defined as a unit that results in polycarbonate oligomers with a number average molecular weight of less than or equal to about 12 or 13 kDalton (polystyrene basis). A polymerization unit is herein defined as a polymerization unit that produces polycarbonate with a number average molecular weight of greater than about 12 or 13 kDalton (polystyrene basis). It is noted that while less than or equal to about 12 or 13 kDalton (polystyrene basis) is used here to define a molecular weight achieved in the first stage, one skilled in the art will readily understand that said molecular weight is used to define an oligomerization stage where the oligomer molecular weight could be greater than 12 kDalton (polystyrene basis). The Fries level in oligomerization reactors may be below 200 ppm or 250 ppm for an intermediate product having a weight of 7-15 kDalton.

A "staged" polymerization reaction condition can be used in continuous polymerization systems, wherein the starting monomers are oligomerized in a first reaction vessel and the oligomeric polycarbonate formed therein is continuously transferred to one or more downstream reactors in which the oligomeric polycarbonate is converted to high molecular weight polycarbonate.

In an exemplary oligomerization stage the oligomeric polycarbonate produced may have a number average molecular weight of from about 1,000 to about 7,500 or even about 13,000 Dalton (polystyrene basis). In an exemplary polymerization stage, the number average molecular weight (Mn) of the polycarbonate may increase to, for example, between about 13,000 and 25,000 Dalton (polystyrene basis), e.g., 13,000 to 18,000 Dalton (polystyrene basis).

After a final polymerization vessel (also referred to as a final polymerization unit), polymer can be introduced to a reactor, extruded, subjected to filtration in a melt filter, or a combination comprising one or more of the foregoing.

The polymerization process (which may be performed via reactor chain) can comprise a section of parallel polymerization, where parallel polymerization refers to the splitting of a polymerized polycarbonate stream into two or more streams that may or may not experience the same polymerization conditions thereafter (i.e., they can attain different molecular weights, have different additives added thereto, and the like). For example, polycarbonate can be prepared in a first portion of the polymerization process; a stream comprising polymerized polycarbonate can be split into two or more streams and directed to 2 or more parallel operating lines. For example, a process can comprise polymerizing polycarbonate in a series of oligomerization units; a stream exiting the first stage can be split into two streams: A and B, where stream A is directed to a polymerization unit A and stream B is directed to a polymerization unit B. Likewise, a process can comprise polymerizing polycarbonate in a series of oligomerization units followed by polymerizing in a series of polymerization units; a stream exiting the second stage can be split into two streams: A and B, where stream A is directed to extruder A and stream B is directed to extruder B. Likewise, a process can comprise polymerizing polycarbonate in a series of oligomerization units followed by polymerizing in a series of polymerization units; a stream exiting the first polymerization unit can be split into two streams: A and B, where stream A is directed to second polymerization unit A and stream B is directed to second stage polymerization unit B. In any of the aforementioned scenarios, a quencher composition can be added to one or both of streams A and B, where the quencher composition can be the same or different. One skilled in the art can readily envision other embodiments comprising more than two parallel streams and embodiments where the streams are split at different locations.

A catalyst used in the melt transesterification polymerization production of polycarbonate may include an alpha catalyst. In some embodiments, the catalyst includes an alpha catalyst and/or a reduced activity alpha catalyst and a beta catalyst, e.g., a beta catalyst that comprises TPPA. It should be understood that any catalyst may comprise one type of molecule, but may also comprise two, three, or more different kinds of molecules.

As used herein, a "reduced activity alpha catalyst" refers to an alpha catalyst comprising a first alpha catalyst and a second alpha catalyst and/or any reaction product thereof and wherein the reduced alpha catalyst has a reduced activity as compared to an alpha catalyst consisting of only the first alpha catalyst. For example, a reduced activity alpha catalyst can have a reduced activity as compared to an alpha catalyst consisting of only the first alpha catalyst under the same melt polymerization conditions in the melt polymerization of polycarbonate.

The alpha catalyst can comprise a source of alkali and/or alkaline earth ions. The sources of these ions include alkali metal hydroxides such as lithium hydroxide, sodium hydroxide, and potassium hydroxide, as well as alkaline earth hydroxides such as magnesium hydroxide and calcium hydroxide. Other sources of alkali and alkaline earth metal ions include the corresponding salts of carboxylic acids (such as sodium acetate) and derivatives of ethylene diamine tetraacetic acid (EDTA) (such as EDTA tetrasodium salt, and EDTA magnesium disodium salt). Other alpha transesterification catalysts include alkali or alkaline earth metal salts of carbonate, such as $Cs_2CO_3$, $NaHCO_3$, and $Na_2CO_3$, and the like, non-volatile inorganic acid such as $NaH_2PO_3$, $NaH_2PO_4$, $Na_2HPO_3$, $KH_2PO_4$, $CsH_2PO_4$, $Cs_2HPO_4$, and the like, or mixed salts of phosphoric acid, such as $NaKHPO_4$, $CsNaHPO_4$, $CsKHPO_4$, and the like. Combinations comprising one or more of the foregoing catalysts can be used.

The reduced activity alpha catalyst can comprise a first alpha catalyst and a second alpha catalyst and/or any reaction product thereof. The first alpha catalyst comprises a source of alkali or alkaline earth ions, where the total amount of alkali ions and alkaline earth ions present in the first alpha catalyst is herein referred to as the "first element," where the first element is the total amount of lithium, sodium, potassium, cesium, rubidium, magnesium, calcium, and strontium present from the first alpha catalyst. Sources of these ions include alkali metal hydroxides such as lithium hydroxide, sodium hydroxide, barium hydroxide, strontium hydroxide, and potassium hydroxide, as well as alkaline earth hydroxides such as magnesium hydroxide and calcium hydroxide.

Other possible sources of alkali and alkaline earth metal ions include the corresponding salts of carboxylic acids (such as sodium acetate, potassium acetate, lithium acetate, calcium acetate, barium acetate, magnesium acetate, and strontium acetate) and derivatives of ethylene diamine tetra acetic acid (EDTA) (such as EDTA tetra sodium salt, and EDTA magnesium disodium salt). The first alpha catalyst can comprise alkali or alkaline earth metal salts of carbonate, such as $Cs_2CO_3$, sodium bicarbonate ($NaHCO_3$), sodium carbonate ($Na_2CO_3$), potassium bicarbonate, lithium bicarbonate, calcium bicarbonate, barium bicarbonate, magnesium bicarbonate, strontium bicarbonate, potassium carbonate, lithium carbonate, calcium carbonate, barium carbonate, magnesium carbonate, strontium carbonate, and the like. The first alpha catalyst can comprise lithium stearate, sodium stearate, strontium stearate, potassium stearate, lithium hydroxyborate, sodium hydroxyborate, sodium phenoxyborate, sodium benzoate, potassium benzoate, lithium benzoate, disodium hydrogen phosphate, dipotassium hydrogen phosphate, dilithium hydrogen phosphate, disodium salts of bisphenol A, dipotassium salts of bisphenol A, and dilithium salts of bisphenol A, sodium salts of phenol, potassium salts of phenol, lithium salts of phenol, or a combination comprising one or more of the foregoing. The first alpha catalyst can comprise a combination comprising one or more of the foregoing first alpha catalysts.

As described elsewhere herein, a user may use a second alpha catalyst. A second alpha catalyst may comprise a non-volatile inorganic acid, where the term "non-volatile" as used herein means that the acid from which the catalyst is made has no appreciable vapor pressure under melt polymerization conditions. Examples of non-volatile acids include phosphorous acid, phosphoric acid, sulfuric acid, and metal "oxo acids" such as the oxo acids of germanium, antimony, niobium and the like. Salts of non-volatile acids include alkali metal salts of phosphites; alkaline earth metal salts of phosphites; alkali metal salts of phosphates; alkaline earth metal salts of phosphates, alkali metal salts of sulfates, alkaline earth metal salts of sulfates, alkali metal salts of metal oxo acids, and alkaline earth metal salts of metal oxo acids. Specific examples of salts of non-volatile acids include $NaH_2PO_3$, $NaH_2PO_4$, $Na_2HPO_4$, $KH_2PO_4$, $CsH_2PO_4$, $Cs_2HPO_4$, $NaKHPO_4$, $NaCsHPO_4$, $KCsHPO_4$, $Na_2SO_4$, $NaHSO_4$, $NaSbO_3$, $LiSbO_3$, $KSbO_3$, $Mg(SbO_3)_2$, $Na_2GeO_3$, $K_2GeO_3$, $Li_2GeO_3$, $MgGeO_3$, $Mg_2GeO_4$, and combinations comprising one or more of the foregoing compounds. The second alpha catalyst may comprise a second element, where the second element is equal to total amount of alkali ions, alkaline earth ions, and metal ions present from the second alpha catalyst, for example, sodium, potassium, cesium, lithium, antimony, magnesium, and germanium. It should be understood that the alpha catalyst may include one, two, or more types of molecules.

The reduced alpha catalyst can comprise a mixture of a first alpha catalyst of NaOH and second alpha catalyst of $KH_2PO_4$. Such a catalyst is referred to herein as $KNaHPO_4$. The reduced activity alpha catalyst can have a molar ratio of the first element to the second element (for example, of the Na from NaOH to K from KH$_2$PO$_4$) of 0.5 to 1.5, specifically, 0.7 to 1.2, for example, 1.0.

A reduced activity alpha catalyst can be prepared by first dissolving second alpha catalyst in water to form a first solution. The first solution can comprise, for example, 100 to 4,000, specifically, 1,500 to 2,000 grams of the second alpha catalyst in 20 liters of water. Meanwhile, a second solution can be prepared by dissolving first alpha catalyst in water and allowing the second solution to cool. The second solution can comprise 50 to 3,000, specifically, 800 to 950 grams of the first alpha catalyst 50 wt % solution in 1 liter of water. The second solution is then added to the first solution to form the reduced alpha catalyst solution. The reduced alpha catalyst solution can be titrated to confirm that the reduced alpha catalyst solution comprises 0 to 20,000, specifically, 100 to 10,000 ppm, of free second (alpha) catalyst, for example, free KH$_2$PO$_4$. The reduced alpha catalyst solution can be combined with additional water, for example with 500 to 4,000 kg, specifically, 1,000 to 1,500 kg of water in an alpha catalyst tank prior to addition to the polymerization unit. The feed rate of the diluted solution can be 0.1 to 10 kilograms per hour (kg/h), specifically, 1 to 5 kg/h into the polymerization unit based on a total monomer feed (i.e., the reactant feed) of 10,000 to 20,000 kg/h, specifically, 12,000 to 15,000 kg/h into the polymerization unit and a total bisphenol A feedrate of 5,000 to 9,000 kg/h of dihydroxy monomer to the polymerization unit. For example, the flow rate of the diluted solution can be 0.1 to 10 kg/h, specifically, 1 to 5 kg/h, more specifically, 2 to 3 kg/h into the polymerization unit based on a total monomer feed of 14,200 kg/h, wherein 7,250 kg/h of the monomer feed is a dihydroxy monomer. The diluted solution can be added to a monomer stream to form a catalyst stream and adding the catalyst stream to a polymerization unit. Likewise, diluted solution can be added to a polymerization at any stage in the polymerization, for example, upstream of, and/or directly to, and/or after a monomer mixing unit; and/or upstream of, and/or directly to, and/or after a polymerization unit (for example, to an oligomerization unit and/or after a final polymerization unit).

Some beta catalysts may be volatile and degrade at elevated temperatures. Beta catalysts can be used at low-temperature polymerization stages (e.g., early in the polymerization process). The beta catalyst may comprise, e.g., TPPA or TPPP, and may also comprise a further beta catalyst such a quaternary ammonium compound, as a second quaternary phosphonium compound, or a combination comprising at least one of the foregoing. As described elsewhere herein, a beta catalyst may comprise an onium salt. Some suitable onium salts include, e.g., tetramethyl phosphonium acetate, tetrapropyl phosphonium acetate, tetrabutyl phosphonium acetate, or tetraphenyl phosphonium acetate.

One suitable beta catalyst comprises TPPA. Another suitable beta catalyst comprises TPPP. A beta catalyst (e.g., TPPA, TPPP) may comprise a further beta catalyst such a quaternary ammonium compound, a second quaternary phosphonium compound, or a combination comprising at least one of the foregoing. As one example, an illustrative beta catalyst may comprise TPPA, TPPP, and a first quaternary ammonium compound.

The quaternary ammonium compound can be a compound of the structure $(R^4)_4N^+X^-$, wherein each $R^4$ is the same or different, and is a $C_{1-20}$ alkyl, a $C_{4-20}$ cycloalkyl, or a $C_{4-20}$ aryl; and $X^-$ is an organic or inorganic anion, for example, a hydroxide, halide, carboxylate, sulfonate, sulfate, formate, carbonate, or bicarbonate. Examples of organic quaternary ammonium compounds include tetramethyl ammonium hydroxide, tetrabutyl ammonium hydroxide, tetramethyl ammonium acetate, tetramethyl ammonium formate, tetrabutyl ammonium acetate, and combinations comprising at least one of the foregoing. The beta catalyst can be free of a quaternary ammonium compound, for example, free of TMAOH.

The quaternary phosphonium compound can be a compound of the structure $(R^5)_4P^+X^-$, wherein each $R^5$ is the same or different, and is a $C_{1-20}$ alkyl, a $C_{4-20}$ cycloalkyl, or a $C_{4-20}$ aryl; and $X^-$ is an organic or inorganic anion, for example, a hydroxide, phenoxide, halide, carboxylate such as acetate or formate, sulfonate, sulfate, formate, carbonate, or bicarbonate. Where $X^-$ is a polyvalent anion such as carbonate or sulfate, it is understood that the positive and negative charges in the quaternary ammonium and phosphonium structures are properly balanced.

The beta catalyst can be added to the polymerization unit in a solution of water, for example, in a solution of 10 to 80 wt %, specifically, 30 to 50 wt %, for example 40 wt % of beta catalyst in water.

The amount of alpha catalyst and beta catalyst used may be based upon the total number of moles of dihydroxy compound used in the polymerization reaction. When referring to the ratio of beta catalyst to all dihydroxy compounds used in the polymerization reaction, it is convenient to refer to moles of catalyst per mole of the dihydroxy compound, meaning the number of moles of catalyst divided by the sum of the moles of each individual dihydroxy compound present in the reaction mixture. In some embodiments, the alpha catalyst can be used in an amount of 0.01 micromoles (μmole, also referred to as microequivalent or μeq) to 30 μeq, specifically, 0.05 μeq to 20 μeq, and more specifically, 0.1 μeq to 10 μeq per mole of the dihydroxy compound used. The amount of beta catalyst (e.g., TPPA) can be 0.1 μeq to 100 μeq, specifically 5 μeq to 90 μeq and more specifically, 20 μeq to 80 μeq (in other words, $2\times10^{-5}$ to $8\times10^{-5}$ moles) per total mole of the dihydroxy compound in the reaction mixture, for example, 50 micromoles of the beta catalyst per mole of dihydroxy monomer. In some embodiments, the beta catalyst (e.g., TPPA, TPPP) is present at from about 1 to about 1000 umol per mol of the dihydroxy compound , or from about 5 to about 200 umol of beta catalyst per mol of the dihydroxy compound.

In some embodiments, the alpha catalyst is used in an amount sufficient to provide $1\times10^{-2}$ to $1\times10^{-8}$ moles, specifically, $1\times10^{-4}$ to $1\times10^{-7}$ moles of metal per mole of the dihydroxy compounds used. The amount of beta catalyst (e.g., organic ammonium or phosphonium salts) may be $1\times10^{-2}$ to $1\times10^{-5}$, specifically $1\times10^{-3}$ to $1\times10^{-4}$ moles per total mole of the dihydroxy compounds used.

The amount of metal (i.e., sodium, potassium, cesium) present may depend upon the metal compound utilized. For example, the beta catalyst can comprise one or more of less than or equal to 2000 ppm of sodium, specifically, less than or equal to 1675 ppm of sodium, specifically, less than or equal to 500 ppm of sodium, more specifically, less than or equal to 100 ppm of sodium, even more specifically, less than or equal to 30 ppm of sodium; less than or equal to 500 ppm of cesium, specifically, less than or equal to 300 ppm of cesium, more specifically, less than or equal to 135 ppm of cesium; and less than or equal to 100 ppm of potassium, specifically, less than or equal to 45 ppm of potassium based on the total weight of the TPPA beta catalyst. In embodiments where the beta catalyst comprises a sodium sulfate, the amount of sodium may be 0 to 1,690 parts per million by weight (ppm), specifically, 0 to 1,671 ppm. If the compound comprises a cesium sulfate, the amount of cesium may be 0 to 275 ppm, specifically, 0 to 252 ppm. If the compound comprises a sodium hydroxide, the amount of sodium is 0 to 35 ppm, specifically, 0 to 29 ppm. If the compound comprises a potassium hydroxide, the amount of potassium is 0 to 50 ppm, specifically, 0 to 43 ppm. If the compound comprises a cesium hydroxide, the amount of cesium is 0 to 140 ppm, specifically, 0 to 132 ppm. Therefore, when using TPPA (for example), the type of metal compound can be determined, and then the amount of the metal present can be adjusted accordingly.

A beta catalyst may have a reduced concentration of metal compounds. For example, the catalyst can comprise one or more of: a) less than or equal to 2,000 ppm of sodium, specifically, less than or equal to 1,675 ppm of sodium, specifically, less than or equal to 500 ppm of sodium, more specifically, less than or equal to 100 ppm of sodium, even more specifically, less than or equal to 30 ppm of sodium; b) less than or equal to 500 ppm of cesium, specifically, less than or equal to 300 ppm of cesium, more specifically, less than or equal to 135 ppm of cesium; and c) less than or equal to 100 ppm of potassium, specifically, less than or equal to 45 ppm of potassium; based on the total weight of the beta catalyst.

For example, the beta catalyst can comprise an alkali metal compound, wherein the amount of sodium can be greater than or equal to 1 ppm, or greater than or equal to 30 ppm, or greater than or equal to 100 ppm; the amount of cesium can be greater than or equal to 10 ppm, or greater than or equal to 30 ppm, or greater than or equal to 50 ppm; the amount of potassium can be greater than 0 ppm, or greater than or equal to 5 ppm, or greater than or equal to 10 ppm; or a combination comprising one or more of the foregoing, wherein the metal amounts are based on the weight of the beta catalyst.

Quenching the transesterification catalysts and any reactive catalyst residues with an acidic compound after polymerization is completed can also be useful in some melt polymerization processes. Removal of catalyst residues and/or quenching agent and other volatile residues from the melt polymerization reaction after polymerization can also be useful in some melt polymerization processes.

The alpha catalyst can be added to a polymerization at any stage in the polymerization, for example, upstream of, and/or directly to, and/or after a monomer mixing unit; and/or upstream of, and/or directly to, and/or after a polymerization unit (for example, to a first stage polymerization unit and/or after the second reaction stage polymerization unit). The beta catalyst can be added to the polymerization unit upstream of, and/or directly to, and/or after a monomer mixing unit; and/or upstream of, and/or directly to, and/or after a first stage polymerization unit.

A second beta catalyst can likewise be added to the polymerization unit upstream of, and/or directly to, and/or after a monomer mixing unit; and/or upstream of, and/or directly to, and/or after a first stage polymerization unit. It should be understood that a beta catalyst may include one, two, three or more types of molecules.

The beta catalyst can be added to a beta catalyst tank prior to melt polymerizing. Beta catalyst can be continuously directed from the beta catalyst tank to a monomer mixing unit. When the amount of beta catalyst is reduced to an amount, for example to less than or equal to 15 wt %, then a fresh amount of beta catalyst can be added to the beta catalyst tank. Likewise, the beta catalyst can be added in a batch addition step.

One or more steps in the present process can be automated via pre-programmed steps, for example, a catalyst addition step, a quencher addition step, a directing step, and the like. Quencher composition can be added at one or more locations in the present melt preparation of the polycarbonate to reduce the activity of the catalyst. The quencher composition comprises a quenching agent (also referred to herein as a quencher). For example, the quenching agent can comprise a sulfonic acid ester or a such as an alkyl sulfonic ester of the formula $R_1SO_3R_2$ wherein $R_1$ is hydrogen, $C_1$-$C_{12}$ alkyl, $C_6$-$C_{18}$ aryl, or $C_7$-$C_{19}$ alkylaryl, and $R_2$ is $C_1$-$C_{12}$ alkyl, $C_6$-$C_{18}$ aryl, or $C_7$-$C_{19}$ alkylaryl. Examples of alkyl sulfonic esters include benzenesulfonate, p-toluenesulfonate, methylbenzene sulfonate, ethylbenzene sulfonate, n-butyl benzenesulfonate, octyl benzenesulfonate and phenyl benzenesulfonate, methyl p-toluenesulfonate, ethyl p-toluenesulfonate, n-butyl p-toluene sulfonate, octyl p-toluenesulfonate and phenyl p-toluenesulfonate. The sulfonic acid ester can comprise alkyl tosylates such as n-butyl tosylate. Sulfonic acid ester can be present in the quencher in an amount of 0.1 to 10 volume percent (vol %), specifically, 0.1 to 5 vol %, more specifically, 0.5 to 2 vol % based on the total volume of the quencher composition.

A quenching agent can comprise one or more boric acid esters (e.g., $B(OCH_3)_3$, $B(OCH_2CH_3)_3$, and $B(OC_6H_6)_3$), zinc borate, boron phosphate, aluminum stearate, aluminum silicate, zirconium carbonate, zirconium $C_1$-$C_{12}$ alkoxides, zirconium hydroxycarboxylates, gallium phosphide, gallium antimonide, germanium oxide, $C_1$-$C_{32}$ organogermanium compounds, $C_4$-$C_{32}$ tetraorganotin tin compound, $C_6$-$C_{32}$ hexaorganotin compound (e.g., [($C_6H_6O$)Sn($CH_2CH_2CH_2CH_3$)$_2$]O), $Sb_2O_3$, antimony oxide, $C_1$-$C_{32}$ alkylantimony, bismuth oxide, $C_1$-$C_{12}$, alkylbismuth, zinc acetate, zinc stearate, $C_1$-$C_{32}$ alkoxytitanium, and titanium oxide, phosphoric acid, phosphorous acid, hypophosphorous acid, pyrophosphoric acid, polyphosphoric acid, boric acid, hydrochloric acid, hydrobromic acid, sulfuric acid, sulfurous acid, adipic acid, azelaic acid, dodecanoic acid, L-ascorbic acid, aspartic acid, benzoic acid, formic acid, acetic acid, citric acid, glutamic acid, salicylic acid, nicotinic acid, fumaric acid, maleic acid, oxalic acid, benzenesulfinic acid, $C_1$-$C_{12}$ dialkyl sulfates (e.g., dimethyl sulfate and dibutyl sulfate), sulfonic acid phosphonium salts of the formula $(R^aSO_3^-)(PR^b_4)^+$ wherein $R^a$ is hydrogen, $C_1$-$C_{12}$ alkyl, $C_6$-$C_{18}$ aryl, or $C_7$-$C_{19}$ alkylaryl, and each $R^b$ is independently hydrogen, $C_1$-$C_{12}$ alkyl or $C_6$-$C_{18}$ aryl, sulfonic acid derivatives of the formula $A^1$-$(Y^1$—$SO_3X^1)_m$ wherein $A^1$ is a $C_1$-$C_{40}$ hydrocarbon group having a valence of m, $Y^1$ is a single bond or an oxygen atom, $X^1$ is a secondary or tertiary alkyl group of the formula —$CR^{15}R^{16}R^{17}$, a metal cation of one equivalent, an ammonium cation (e.g., $NR^b_3{}^+$ wherein each $R^b$ is independently hydrogen, $C_1$-$C_{12}$ alkyl or $C_6$-$C_{18}$ aryl), or a phosphonium (e.g., $PR^b_4{}^+$ wherein each $R^b$ is independently hydrogen, $C_1$-$C_{12}$ alkyl or $C_6$-$C_{18}$ aryl) wherein $R^{15}$ is a hydrogen atom or an alkyl group having 1 to 5 carbon atoms, $R^{16}$ is a hydrogen atom, a phenyl group or an alky group having 1 to 5 carbon atoms, and $R^{17}$ is the same as or different from $R^{15}$ and has the same definition as $R^{15}$, provided that two of $R^{15}$, $R^{16}$, and $R^{17}$ cannot be hydrogen atoms, and m is an integer of 1 to 4, provided that when $Y^1$ is a single bond, all of $X^1$ in an amount of m cannot be metal cations of one equivalent, a compound of the formula $^+X^2$-$A^2$-$Y^1$—$SO_3^-$ wherein $A^2$ is a divalent hydrocarbon group, $^+X^2$ is a secondary, tertiary or quaternary ammonium cation or a secondary (e.g., tertiary or quaternary phosphonium cation, and $Y^1$ is a single bond or an oxygen atom, a compound of the formula $A^3$-$(^+X^3)_n$.(R—$Y^1$—

$SO_3^-)_n$ wherein $A^3$ is a $C_1$-$C_{40}$ hydrocarbon group having a valence of n, $^+X^3$ is a secondary, tertiary or quaternary ammonium cation (e.g., $NR^b_3{}^+$ wherein each $R^b$ is independently hydrogen, $C_1$-$C_{12}$, alkyl or $C_6$-$C_{18}$ aryl), or a secondary, tertiary or quaternary phosphonium cation (e.g., $PR^b_4{}^+$ wherein each $R^b$ is independently hydrogen, $C_1$-$C_{12}$ alkyl or $C_6$-$C_{18}$ aryl), R is a monovalent $C_1$-$C_{40}$ hydrocarbon group, n is an integer of 2 to 4, and $Y^1$ is a single bond or an oxygen atom, a compound of the formula $A^5$-$Ad^1$-$A^4$-$(Ad^2$-$A^5)_l$ wherein $A^5$ is a monovalent or divalent $C_1$-$C_{40}$ hydrocarbon group, $A^4$ is a divalent $C_1$-$C_{40}$ hydrocarbon group, each of $Ad^1$ and $Ad^2$ is independently an acid anhydride group selected from —$SO_2$—O—$SO_2$—, —$SO_2$—O—CO—, and —CO—O—$SO_2$—, and l is 0 or 1, provided that when l is 0, —$(Ad^2$-$A^5)_l$ is a hydrogen atom or a bond between $A^4$ and $A^5$, in which $A^5$ is a divalent hydrocarbon group or a single bond, aminosulfonic esters having the formula $R_aR_bN$-A-$SO_3R_c$, wherein $R_a$ and $R_b$ are each independently hydrogen, $C_1$-$C_{12}$ alkyl, $C_6$-$C_{22}$ aryl, $C_7$-$C_{19}$ alkylaryl or $R_a$ and $R_b$, either singly or in combination, form an aromatic or non-aromatic heterocyclic compound with N (e.g., pyrrolyl, pyridinyl, pyrimidyl, pyrazinyl, carbazolyl, quinolinyl, imidazoyl, piperazinyl, oxazolyl, thiazolyl, pyrazolyl, pyrrolinyl, indolyl, purinyl, pyrrolydinyl, or the like), $R_c$ is hydrogen, and A is $C_1$-$C_{12}$ alkyl, $C_6$-$C_{18}$ aryl, or $C_{17}$-$C_{19}$ alkylaryl (e.g., compounds such as N-(2-hydroxyethyl) piperazine-N'-3-propanesulfonic acid, 1,4,-piperazinebis (ethanesulfonic acid), and 5-dimethylamino-1-napthalenesulfonic acid), ammonium sulfonic esters of the formula $R_aR_bR_cN^+$-A-$SO_3^-$, wherein $R_a$, $R_b$, are each independently hydrogen, $C_1$-$C_{12}$ alkyl, $C_1$-$C_{12}$ aryl, $C_7$-$C_{19}$ alkylaryl, or $R_a$ and $R_b$, either singly or in combination, form an aromatic or non-aromatic heterocyclic compound with N (e.g., pyrrolyl, pyridinyl, pyrimidyl, pyrazinyl, carbazolyl, quinolinyl, imidazoyl, piperazinyl, oxazolyl, thiazolyl, pyrazolyl, pyrrolinyl, indolyl, purinyl, pyrrolydinyl, or the like), $R_c$ is a hydrogen, and A is $C_1$-$C_{12}$ alkyl, $C_6$-$C_{18}$ aryl, or $C_7$-$C_{19}$ alkylaryl, sulfonated polystyrene, methyl acrylate-sulfonated styrene copolymer, and combinations comprising at least one of the foregoing.

The quencher addition step can comprise mixing the quencher composition with the polymerized polycarbonate for a period of time of greater than or equal to 5 seconds prior to the addition to the polycarbonate of any reactive additive, wherein the reactive additive has a reactive OH group or reactive ester group. As used herein, when referring to "reactive" or a "reactive group", e.g., having a reactive $OH^-$ group or a reactive ester group, the reactivity is with respect to polycarbonate.

An additive can further be added at one or more locations in the present melt preparation of the polycarbonate. The additive can be added as part of the quencher composition or can be added separately. The additive can comprise, for example, an impact modifier, a flow modifier, a filler (e.g., a particulate polytetrafluoroethylene (PTFE), glass, carbon, a mineral, or metal), a reinforcing agent (e.g., glass fibers), an antioxidant, a heat stabilizer, a light stabilizer, an ultraviolet (UV) agent (such as a UV light stabilizer and a UV absorbing additive), a plasticizer, a lubricant, a release agent (such as a mold release agent), an antistatic agent, an antifog agent, an antimicrobial agent, a colorant (e.g., a dye or pigment), a surface effect additive, a radiation stabilizer, a flame retardant, an anti-drip agent (e.g., a PTFE-encapsulated styrene-acrylonitrile copolymer, such as TSAN)), or any combination comprising of one or more of the foregoing. In general, the additives are used in the amounts generally known to be effective. For example, the total amount of the additive composition (other than any impact modifier, filler, or reinforcing agent) can be 0.001 to 10.0 weight percent (wt %), or 0.01 to 5 wt %, each based on the total weight of the polymer in the polymerized composition. Plasticizers, lubricants, and/or mold release agents can also be used.

A quenched composition can be essentially free of chlorine and bromine. "Essentially free of chlorine and bromine" is defined as having a bromine and/or chlorine content of less than or equal to 100 parts per million by weight (ppm), less than or equal to 75 ppm, or less than or equal to 50 ppm, based on the total parts by weight of the composition, excluding any filler. The present polymerization can occur in the presence of or in the absence of a branching agent or in other words, the present process can comprise or can be free of a branching agent addition step.

The polycarbonate composition can have a light transparency of greater than 90% as determined using 3.2 millimeter (mm) thick samples using ASTM D1003-00, Procedure B using CIE standard illuminant C, with unidirectional viewing. Accordingly, when the quenched composition has such a light transparency, it is herein referred to as an "optical grade" composition.

Although transparent polycarbonate is not a requirement, in some embodiments a user may seek to synthesize polycarbonate that is uncolored or nearly uncolored. Although not a requirement, a user may synthesize polycarbonate that has less than about 100, less than 10, or even less than 1 ppb of chlorinated or other halogenated impurities. Without being bound to any particular theory, the presence of such impurities may affect the coloration of the final polycarbonate product. The final polycarbonate product may also have a purity in terms of vanadium, niobium, or other species (e.g., iron) as described elsewhere herein.

The polycarbonate can have a melt flow of less than or equal to 50 cubic centimeters per 10 minutes (cc/10 min), specifically, 3 to 30 cc/10 min as determined at 300° C. and a load of 1.2 kilograms according to ASTM D1238-04.

The polycarbonate can have a melt flow of 4 to 40 grams per 10 minutes (g/10 min), for example, 4.5 to 15 g/10 min or 15 to 35 g/10 min as determined by ASTM D1238-04 at 300° C., 1.2 kg. The polycarbonate can have a melt flow of 5 to 15 g/10 min as determined by ASTM D1238-04 at 250° C., 1.5 kg.

The polycarbonate can be, for example, a bisphenol A polycarbonate with a weight average molecular weight of 20,000 to 40,000 Dalton (polystyrene basis), for example, 21,800 Dalton (polystyrene basis) with a melt flow of 24 to 32 g/10 min (ASTM D1238-04, 300° C., 2.16 kg).

The polycarbonate can, in some embodiments, have a branching level of less than or equal to about 1200 ppm, specifically, less than or equal to 900 ppm, more specifically, less than or equal to about 750 ppm, even more specifically, less than or equal to about 410 ppm based on the total weight of the polycarbonate. In some embodiments, the polycarbonate exhibits a Fries rearrangement level of from about 100 ppm to about 1200 ppm, e.g., from about 150 ppm to about 1150 ppm, from about 250 ppm to about 1100 ppm, from about 450 ppm to about 1050 ppm, from about 500 ppm to about 1000 ppm, from about 550 ppm to about 950 ppm, from about 600 ppm to about 900 ppm, from about 650 ppm to about 850 ppm, from about 700 ppm to about 800 ppm, or even about 750 ppm.

The polycarbonate can have an end cap level of greater than or equal to 60%, specifically, greater than or equal to 70%, more specifically, greater than or equal to 80%, where the end cap level is determined by dividing the total number of end groups of DPC by the total number of end groups (for example, those derived from DPC plus those comprising a —OH group) and multiplying by 100.

The following examples are provided to illustrate the present technology. The examples are illustrative only and do not limit this disclosure to the materials, conditions, or process parameters set forth therein.

Non-Limiting Examples

The following examples are illustrative only; the compositions, process conditions, and reactor configurations/sequence are exemplary only and do not limit the present disclosure.

Melt polymerizations were run in a continuous melt polycarbonate plant, where 58.7 kg/h bisphenol-A (BPA) and 55.1 kg/h of diphenyl carbonate (DPC) were fed into a continuously stirred formulation tank. The formulation tank was operated at atmospheric pressure and 170° C. 75 micromoles of TPPA per mol of BPA were added to the formulation tank. In the case of the operation with TBPA, its addition was done at a rate of 50 micromoles of TBPA per mol of BPA as final concentration in formulation tank.

The outlet stream of the formulation tank was then pumped to a continuously stirred first reactor, which operated at 257° C. and 180 milibar (mbar) vacuum in order to remove the reaction side-product, phenol. The vapor phase containing phenol and unreacted monomers BPA and DPC were continuously distilled in a scrubber where reflux ratio was adjusted so that the column head temperature was 127° C. to yield high purity phenol. Unreacted BPA and DPC were fed back into the first reactor. In order to compensate for the DPC losses in the phenol overhead streams of other reactors, an additional stream of DPC was added to the first reactor at 1.8 kg/h. An aqueous stream of alpha catalyst as defined in each of the examples was added in the first reactor at a flowrate in milliliters per minute (mL/min).

The outlet stream of the first reactor was then pumped to a continuously stirred second reactor, which operated at 280° C. and 37 mbar vacuum. Due to the higher viscosity of this stream, a gear pump was used to convey the stream to the polymerization section where two horizontal polymerizers in series were used to reach the final polymer viscosity. The first polymerizer operated at 300° C. and 2.5 to 3.0 mbar vacuum.

Phenol was removed and the continuous agitation was provided by a spectacle-type blade run at 20 revolutions per minute (rpm). The polymer stream was then pumped to the second polymerizer, which operated at 1.0-1.5 mbar and 302° C. The second polymerizer had a lattice-type agitator. The polymer was then fed from the second polymerizer to a 6 barrel twin screw finishing extruder (length/diameter (L/D)=21, D=44 mm), where the barrel temperature was set at 300° C. and a spin rate of 100 rpm.

Illustrative Data

Several illustrative, non-limiting experiments were performed to test the effect of TPPA impurities. Trials were done using oligomer materials from a melt polycarbonate pilot plant (Melt PC Pilot Plant). Oligomers were produced using standard catalyst package: TBPA (organic catalyst) and NaKHPO$_4$ (inorganic catalyst). This material was spiked with TPPO and Triphenyl phosphine (TPP). The spiked oligomer samples were further polymerized in laboratory polymerizers by submitting them to temperature and vacuum for 60 minutes to simulate the polymerization process in the plant. Under these conditions, the TPP and TPPO contents were under control and could be easily modified. The pilot plant performed runs operating at 42 kg/h with different loadings of beta and alpha catalysts. The TPPA lots used contained different contents of Na and of TPPO, both as impurities. Table 1 (below) summarizes selected characteristics of the TPPA lots used, including sodium content in sample TPPA lots sourced and tested in Melt PC pilot plant. The last two columns summarize TPPA purity and TPPO amount present in each sample.

TABLE 1

| Laboratory polymerizations | | | |
| --- | --- | --- | --- |
| Lot | Na content [ppm] | TPPA [wt %] | TPPO [wt %] |
| 1 | 20 | 99.72% | 0.280% |
| 2 | 93 | 99.16% | 0.841% |
| 3 | 56 | 98.24% | 1.759% |
| 4 | 17 | 98.81% | 1.194% |
| 5 | 17 | | |
| 6 | 50 | 99.23% | 0.771% |
| 7 | 3 | 99.02% | 0.982% |

Figure 1:
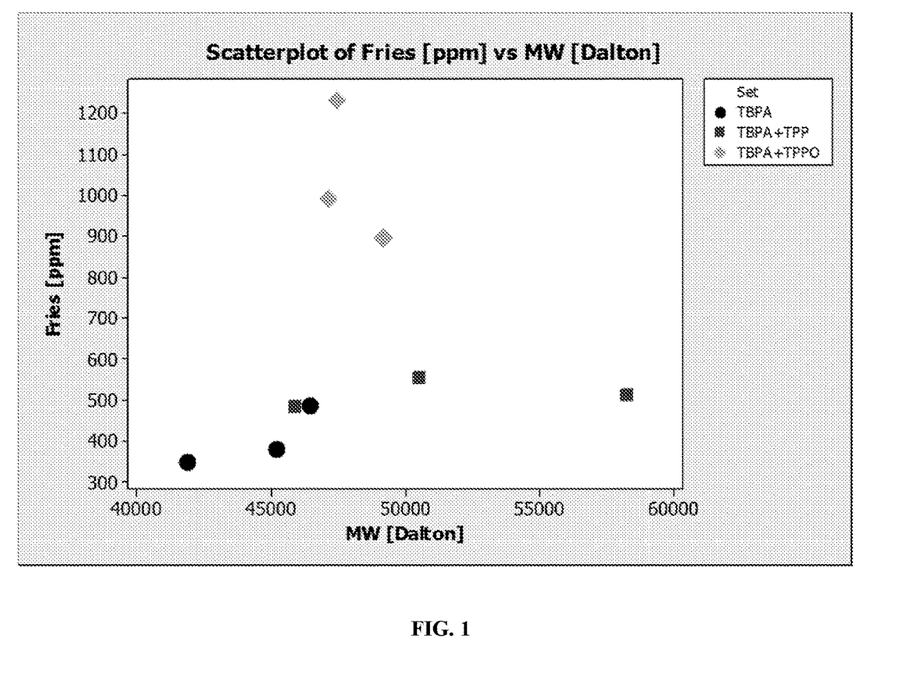
FIG. 1 provides the results of Fries level and molecular weight obtained in laboratory polymerizations.

A first set of experiments was performed using oligomer materials from the Melt PC pilot plant. Initially, oligomer materials were post-polymerized in the laboratory polymerizers without any spiking. Polymer obtained showed Fries levels in the range of 400 ppm. When oligomer materials were spiked with 100 ppm of TPPO or TPP the amount of Fries increased. In the case of TPPO, the amount of Fries doubled up to 1000 ppm, while in the case of TPP the value reached 500 ppm and is not significantly different than the level obtained without spike. Table 2 (laboratory polymerization average results using oligomerization section material from pilot plant and spike of 100 ppm of TPPO or TPP) and FIG. 1 summarize the results:

TABLE 2

| Set | Fries [ppm] | MW [kDa] |
| --- | --- | --- |
| No Spike (TBPA) | 406 | 44.46 |
| Spike TPPO | 1041 | 47.89 |
| Spike TPP | 517 | 51.54 |

A 100 ppm spike of TPPO or TPP corresponds to a content of 91.4 umol TPPO/mol BPA or 96.9 umol TPP/mol BPA in the sample being considered. These results are surprising because the results show the opposite trend expected on the estimated/proposed catalytic activity mechanisms proposed based on TPP and TPPO's basicity.

Pilot Plant Polymerizations

A second set of experiments was carried out in the Melt PC pilot plant. Along the different runs performed in the pilot plant using similar loadings of beta catalyst (75-40 umol) and similar loadings of alpha catalyst (35-40 ppb) two different sets can be distinguished.

Figure 2:
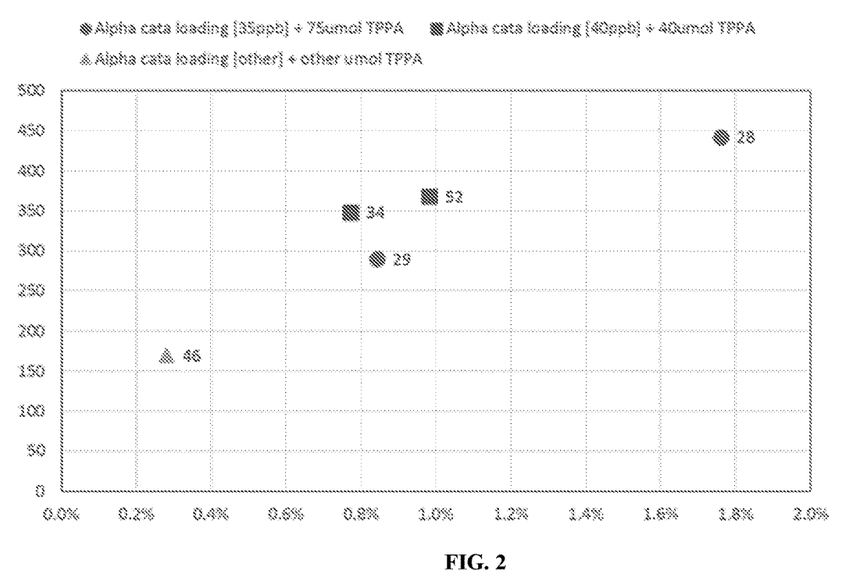
FIG. 2 provides Results of Fries level [ppm] in oligomerization reactor against TPPO wt % content in TPPA used. Number in plot shows run number shown in Table 3.
Figure 3:
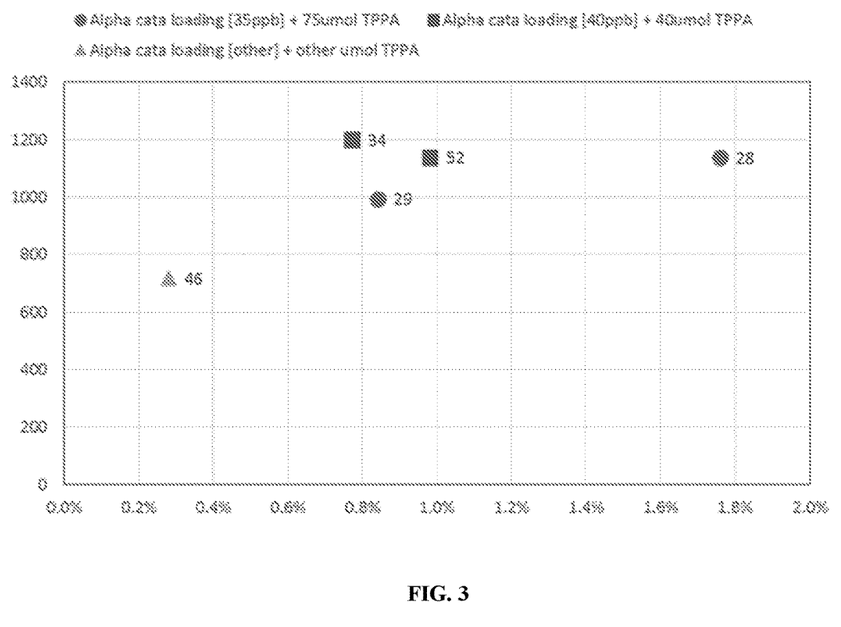
FIG. 3 provides Results of Fries level [ppm] in final product against TPPO wt % content in TPPA used. Number in the plot is run number shown in Table 3 below, which table provides pilot plant results for MW and Fries rearrangement level in oligomerization section and in final product. For reference, the table also includes the amount of Na and TPPO present in a given tested lot.

In order to study the effect of the different TPPA lots, samples of both oligomers and final product sample were collected and MW and Fries level on those samples were analyzed. FIGS. 2 and 3 summarize the results reported in Table 3, showing trends in the Fries buildup in the oligomerization section reactor and in the final product.

TABLE 3

| Lot | Internal run code | TPPA loading [umol] | Alfa cata loading [ppb Na] | Final Product MW [kDa] | Final product Fries [ppm] | Oligomer MW [kDa] | Oligomer Fries [ppm] | TPPO [wt %] | Lot Na content [ppm] |
|---|---|---|---|---|---|---|---|---|---|
| 1 | 46 | 50 | 22 | 58.0 | 717  | 11.0 | 170 | 0.280% | 20 |
| 2 | 29 | 75 | 35 | 58.2 | 995  | 11.6 | 290 | 0.841% | 93 |
| 3 | 28 | 75 | 35 | 58.7 | 1137 | 11.5 | 442 | 1.759% | 56 |
| 4 | 24 | 75 | 35 | 55.7 | 535  | 11.4 | 197 | 1.194% | 17 |
| 5 | 15 | 75 | 40 | 54.4 | 534  | —    | —   |        | 17 |
| 6 | 34 | 40 | 40 | 59.7 | 1200 | 11.2 | 348 | 0.771% | 50 |
| 7 | 52 | 40 | 40 | 59.2 | 1139 | 11.0 | 368 | 0.982% | 3  |

With respect to oligomer samples in FIG. 2, the runs performed at 75 umol of TPPA and 35 ppb of Na (round dot markers), show a slight trend in that larger amount of Fries levels in the oligomerization section are obtained with lots which had higher TPPO content. Similarly in the case of the runs performed at 40umol of TPPA and 40 ppbs of Na. Run #46 showed the lowest amount of Fries in the oligomerization section and also contained the lowest amount of TPPO. Considering final product samples, FIG. 3, the runs performed at 75 umol of TPPA and 35 ppb of Na, also show a slight trend in Fries.

Based on the former results from laboratory and the oligomerization section measurements in the pilot plant—and without being bound to any particular theory—the content of TPPO in TPPA affects the production of Fries in an oligomerization stage and potentially also in the final product, and one may consider placing limits on TPPO content. One such value may be that of lot 1 (0.280 wt %), which made the level of Fries in an oligomerization stage similar to values similar to TBPA.

In general, the disclosed technology may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention. Set forth below are exemplary embodiments of the process and polymerized polycarbonate disclosed herein.

Aspect 1. A polymerization process, comprising: melt polymerizing a carbonate and a dihydroxy compound in the presence of an amount of a beta organic catalyst so as to give rise to a polycarbonate product, wherein the amount of beta organic catalyst comprises at least one onium salt and also comprises triphenyl phosphonium oxide (TPPO), and wherein the TPPO represents less than about 0.3 weight % of the sum of the weights of the at least one onium salt and the TPPO in the amount of beta organic catalyst.

Aspect 2. The polymerization process of aspect 1, wherein the onium salt comprises tetramethyl phosphonium acetate, tetrapropyl phosphonium acetate, tetrabutyl phosphonium acetate, or tetraphenyl phosphonium acetate. Tetraphenyl phosphonium acetate is considered especially suitable.

Aspect 3. The polymerization process of aspect 1, wherein the TPPO represents less than about 0.2 weight % of the sum of the weights of the at least one onium salt and TPPO in the amount of beta organic catalyst.

Aspect 4. The polymerization process of aspect 1, wherein the melt polymerizing is performed in the presence of an alpha inorganic catalyst that comprises one or more alkali metal salts, one or more alkaline earth metal salts, or any combination thereof.

Aspect 5. The polymerization process of aspect 4, wherein the alpha inorganic catalyst comprises lithium hydroxide, sodium hydroxide, barium hydroxide, strontium hydroxide, potassium hydroxide, magnesium hydroxide, calcium hydroxide, sodium acetate, potassium acetate, lithium acetate, calcium acetate, barium acetate, magnesium acetate, strontium acetate, EDTA tetra sodium salt, EDTA magnesium disodium salt, Cs2CO3, sodium bicarbonate ($NaHCO_3$), sodium carbonate ($Na_2CO_3$), potassium bicarbonate, lithium bicarbonate, calcium bicarbonate, barium bicarbonate, magnesium bicarbonate, strontium bicarbonate, potassium carbonate, lithium carbonate, calcium carbonate, barium carbonate, magnesium carbonate, strontium carbonate, lithium stearate, sodium stearate, strontium stearate, potassium stearate, lithium hydroxyborate, sodium hydroxyborate, sodium phenoxyborate, sodium benzoate, potassium benzoate, lithium benzoate, disodium hydrogen phosphate, dipotassium hydrogen phosphate, dilithium hydrogen phosphate, disodium salts of bisphenol A, dipotassium salts of bisphenol A, and dilithium salts of bisphenol A, sodium salts of phenol, potassium salts of phenol, lithium salts of phenol, $NaH_2PO_3$, $NaH_2PO_4$, $Na_2HPO_4$, $KH_2PO_4$, $CsH_2PO_4$, $Cs_2HPO_4$, $NaKHPO_4$, $NaCsHPO_4$, $KCsHPO_4$, $Na_2SO_4$, $NaHSO_4$, $NaSbO_3$, $LiSbO_3$, $KSbO_3$, $Mg(SbO_3)_2$, $Na_2GeO_3$, $K_2GeO_3$, $Li_2GeO_3$, $MgGeO_3$, $Mg_2GeO_4$, or any combination thereof.

Aspect 6. The polymerization process of aspect 5, wherein the alpha inorganic catalyst comprises $NaKHPO_4$.

Aspect 7. The polymerization process of aspect 1, wherein the polycarbonate product is an oligomerization product having an average molecular weight of less than or equal to about 13 kDalton (polystyrene basis) and wherein the oligomerization product exhibits a Fries rearrangement level of less than about 500 ppm. Fries rearrangement levels of below about 500 ppm are considered suitable; Fries rearrangement levels of below about 300 ppm, below about 275 ppm, below about 250 ppm, below about 225 ppm, or even below about 200 ppm are also suitable.

An oligomerization product may have a Fries level in the range of, e.g., from about 150 to about 500 ppm, e.g., from about 175 to about 475 ppm, from about 200 to about 450 ppm, from about 225 to about 425 ppm, from about 250 to about 400 ppm, from about 275 to about 375 ppm, from about 300 to about 350 ppm, or even about 325 ppm.

Aspect 8. The polymerization process of aspect 1, wherein the polycarbonate product is a polymerization product having an average molecular weight of more than about 13 kDalton (polystyrene basis) and wherein the polymerization product exhibits a Fries rearrangement level of from about 100 ppm to about 1200 ppm, e.g., from about 150 ppm to about 1150 ppm, from about 250 ppm to about 1100 ppm, from about 450 ppm to about 1050 ppm, from about 500 ppm to about 1000 ppm, from about 550 ppm to about 950 ppm, from about 600 ppm to about 900 ppm, from about 650 ppm to about 850 ppm, from about 700 ppm to about 800 ppm, or even about 750 ppm.

Aspect 9. The polymerization process of aspect 2, wherein the beta catalyst comprises tetraphenyl phosphonium acetate, and the tetraphenyl phosphonium acetate is present during the reacting at from about 5 to about 200 umol of tetraphenyl phosphonium acetate per mol of the dihydroxy compound.

Aspect 10. The polymerization process of aspect 1, wherein the carbonate comprises diphenyl carbonate, and wherein the dihydroxy compound comprises bisphenol A.

Aspect 11. The polymerization process of aspect 1, wherein the beta catalyst comprises an amount of metal and wherein the amount of metal present is based upon the weight of the catalyst compound is present, wherein the metal comprises at least one of sodium, potassium, cesium; and wherein: if the compound comprises a sodium sulfate, the amount of sodium is 0 to 1,690 ppm; if the compound comprises a cesium sulfate, the amount of cesium is 0 to 275 ppm; if the compound comprises a sodium hydroxide, the amount of sodium is 0 to 35 ppm; if the compound is a potassium hydroxide, the amount of potassium is 0 to 50 ppm; and/or if the compound comprises a cesium hydroxide, the amount of cesium is 0 to 140 ppm.

In some embodiments, the beta catalyst comprises an amount of metal, the metal comprises at least one of sodium, potassium, cesium; and wherein (the amount of metal present is based upon which compound is present): if the compound comprises a sodium sulfate, the amount of sodium is 0 to 1,671 ppm; if the compound comprises a cesium sulfate, the amount of cesium is 0 to 252 ppm; if the compound comprises a sodium hydroxide, the amount of sodium is 0 to 29 ppm; if the compound is a potassium hydroxide, the amount of potassium is 0 to 43 ppm; and/or if the compound comprises a cesium hydroxide, the amount of cesium is 0 to 132 ppm.

Aspect 12. The polymerization process of any of aspects 1-11, further comprising adding a quencher composition.

Aspect 13. A polycarbonate composition made according to any of aspects 1-12.

Aspect 14. A polymerization process, comprising: (a) melt polymerizing in a first stage a carbonate and a dihydroxy compound in the presence of an amount of a beta organic catalyst so as to give rise to a polycarbonate oligomer product, wherein the amount of beta organic catalyst comprises at least one onium salt and also comprises triphenyl phosphonium oxide (TPPO), wherein the TPPO represents less than about 0.3 weight % of the sum of the weights of the at least one onium salt and the TPPO in the amount of beta organic catalyst, and wherein the polycarbonate oligomer product has an average molecular weight of less than or equal to about 13 kDalton (polystyrene basis) and exhibiting a Fries rearrangement level of less than about 500 ppm; b) reacting in a second stage the polycarbonate oligomer product and optionally a carbonate and a dihydroxy compound in the presence of an amount of a beta organic catalyst so as to give rise to a polycarbonate polymerized product, wherein the amount of beta organic catalyst comprises at least one onium salt and triphenyl phosphonium oxide (TPPO), and wherein the TPPO represents less than about 0.3 weight % of the sum of the weights of the at least one onium salt and the TPPO in the amount of beta organic catalyst, and wherein the polycarbonate polymerized product has an average molecular weight of more than about 13 kDalton (polystyrene basis) and wherein the polymerization product exhibits a Fries rearrangement level of from about 100 ppm to about 1200 ppm.

Aspect 15. The polymerization process of aspect 14, wherein the beta catalyst is present during the first stage, the second stage, or both, at from about 5 to about 200 umol of beta catalyst per mol of the dihydroxy compound, e.g., BPA. Beta catalyst may be present at, e.g., from about 15 to about 80 umol/mol of BPA, or from about 20 to about 70 umol/mol BPA, or from about 25 to about 65 umol/mol BPA, or from about 30 to about 60 umol/mol BPA, or from about 35 to about 55 umol/mol BPA, or from about 40 to about 45 umol/mol BPA.

Aspect 16. The process of any of aspects 14-15, further comprising adding a quencher composition to the polycarbonate.

Aspect 17. The process of aspect 16, further comprising adding the quencher composition at a pressure of greater than or equal to about 2 bars.

Aspect 18. The process of any of aspects 14-17, further comprising mixing the quencher composition with the polycarbonate for greater than or equal to 5 seconds before adding to the polycarbonate additives having a reactive OH or reactive ester group.

Aspect 19. The process of any of aspects 14-18, wherein the beta catalyst comprises an amount of metal and wherein the amount of metal present is based upon which compound is present, wherein the metal comprises at least one of sodium, potassium, cesium; and wherein: if the compound comprises a sodium sulfate, the amount of sodium is 0 to 1,690 ppm; if the compound comprises a cesium sulfate, the amount of cesium is 0 to 275 ppm; if the compound comprises a sodium hydroxide, the amount of sodium is 0 to 35 ppm; if the compound is a potassium hydroxide, the amount of potassium is 0 to 50 ppm; and/or if the compound comprises a cesium hydroxide, the amount of cesium is 0 to 140 ppm.

Aspect 20. The process of aspect 19, wherein the beta catalyst comprises an amount of metal and wherein the amount of metal present is based upon which compound is present, wherein the metal comprises at least one of sodium, potassium, cesium; and wherein: if the compound comprises a sodium sulfate, the amount of sodium is 0 to 1,671 ppm; if the compound comprises a cesium sulfate, the amount of cesium is 0 to 252 ppm; if the compound comprises a sodium hydroxide, the amount of sodium is 0 to 29 ppm; if the compound is a potassium hydroxide, the amount of potassium is 0 to 43 ppm; and/or if the compound comprises a cesium hydroxide, the amount of cesium is 0 to 132 ppm.

Aspect 21. A polycarbonate composition made according to any of aspects 14-20 wherein the composition exhibits a Fries rearrangement level of from about 100 ppm to about 1150 ppm, e.g., from about 150 ppm to about 1150 ppm, from about 250 ppm to about 1100 ppm, from about 450 ppm to about 1050 ppm, from about 500 ppm to about 1000 ppm, from about 550 ppm to about 950 ppm, from about 600 ppm to about 900 ppm, from about 650 ppm to about 850 ppm, from about 700 ppm to about 800 ppm, or even about 750 ppm.

Aspect 22. The composition made according to any of aspects 14-20, wherein the composition exhibits a Fries rearrangement level of less than about 300 ppm, e.g., less than about 275, about 250, about 225, about 200, about 175, about 150, about 125, or even less than about 100 ppm, Aspect 23. A system, comprising: a reactor chain configured to synthesize a polycarbonate product; and an amount of beta organic catalyst, wherein the amount of beta organic catalyst comprises at least one onium salt and also comprises TPPO, and wherein the TPPO represents less than about 0.3 weight % of the sum of the weights of the at least one onium salt and the TPPO in the amount of beta organic catalyst.

Aspect 24. The system of aspect 23, further comprising an amount of a carbonate and a dihydroxy compound.

Aspect 25. The system of any of aspects 23-24, further comprising an amount of an alpha inorganic catalyst.

Aspect 26. The system of aspect 25, wherein the alpha inorganic catalyst comprises one or more alkali metal salts, one or more alkaline earth metal salts, or any combination thereof.

Aspect 27. The system of aspect 23, wherein the reactor chain comprises a first stage configured to synthesize polycarbonate oligomerization product having an average molecular weight of less than or equal to about 13 kDalton (polystyrene basis).

Aspect 28. The system of aspect 27, wherein the reactor chain further comprises a second stage configured to synthesize a polycarbonate polymerization product having an average molecular weight of more than about 13 kDalton (polystyrene basis).

Aspect 29. The system of aspect 27, wherein the reactor chain further comprises a second stage configured to synthesize a polycarbonate polymerization product having an average molecular weight of from about 25,000 to 70,000 Dalton (polystyrene basis).

Aspect 30. The system of any of aspects 23-28, wherein the system is configured to synthesize a polycarbonate polymerization product exhibits a Fries rearrangement level of from about 100 ppm to about 1200 ppm, e.g., from about 150 ppm to about 1150 ppm, from about 250 ppm to about 1100 ppm, from about 450 ppm to about 1050 ppm, from about 500 ppm to about 1000 ppm, from about 550 ppm to about 950 ppm, from about 600 ppm to about 900 ppm, from about 650 ppm to about 850 ppm, from about 700 ppm to about 800 ppm, or even about 750 ppm.

Aspect 31. The system of aspect 23, wherein the beta catalyst comprises an amount of metal and wherein the amount of metal present is based upon which compound is present, wherein the metal comprises at least one of sodium, potassium, cesium; and wherein: if the compound comprises a sodium sulfate, the amount of sodium is 0 to 1,690 ppm; if the compound comprises a cesium sulfate, the amount of cesium is 0 to 275 ppm; if the compound comprises a sodium hydroxide, the amount of sodium is 0 to 35 ppm; if the compound is a potassium hydroxide, the amount of potassium is 0 to 50 ppm; and/or if the compound comprises a cesium hydroxide, the amount of cesium is 0 to 140 ppm.

Aspect 32. A polycarbonate composition made by a system according to any of aspects 23-31.

Aspect 33. A system, comprising: a reactor chain configured to synthesize a polycarbonate product; an amount of a carbonate disposed within the reactor chain; an amount of a dihydroxy compound disposed within the reactor chain; and an amount of beta organic catalyst disposed within the reactor chain, wherein the amount of beta organic catalyst comprises at least one onium salt and also comprises triphenyl phosphonium oxide (TPPO), and wherein the TPPO represents less than about 0.3 weight % of the sum of the weights of the at least one onium salt and the TPPO in the amount of beta organic catalyst.

Aspect 34. The system of aspect 33, further comprising an amount of an alpha inorganic catalyst.

Aspect 35. The system of aspect 33, wherein the wherein the alpha inorganic catalyst comprises one or more alkali metal salts, one or more alkaline earth metal salts, or any combination thereof.

Aspect 36. The system of aspect 33, wherein the dihydroxy compound comprises bisphenol A and wherein the carbonate comprises diphenyl carbonate.

Aspect 37. The system of any of aspects 33-36, further comprising a quencher composition disposed within the reactor chain.

Aspect 38. The system of any of aspects 33-37, wherein the system is configured to synthesize a polycarbonate polymerization product that exhibits a Fries rearrangement level of from about 100 ppm to about 1200 ppm, e.g., from about 150 ppm to about 1150 ppm, from about 250 ppm to about 1100 ppm, from about 450 ppm to about 1050 ppm, from about 500 ppm to about 1000 ppm, from about 550 ppm to about 950 ppm, from about 600 ppm to about 900 ppm, from about 650 ppm to about 850 ppm, from about 700 ppm to about 800 ppm, or even about 750 ppm.

Aspect 39. The system of any of aspects 33-37, wherein the system is configured to synthesize a polycarbonate polymerization product that exhibits a Fries rearrangement level less than about 500 ppm. Fries rearrangement levels of below about 500 ppm are considered suitable; Fries rearrangement levels of below about 300 ppm, below about 275 ppm, below about 250 ppm, below about 225 ppm, or even below about 200 ppm are also suitable. An oligomerization product may have a Fries level in the range of from about 150 to about 500 ppm, e.g., from about 175 to about 475 ppm, from about 200 to about 450 ppm, from about 225 to about 425 ppm, from about 250 to about 400 ppm, from about 275 to about 375 ppm, from about 300 to about 350 ppm, or even about 325 ppm.

Aspect 40. The system of aspect 30, wherein the beta catalyst comprises an amount of metal and wherein the amount of metal present is based upon which compound is present, wherein the metal comprises at least one of sodium, potassium, cesium; and wherein: if the compound comprises a sodium sulfate, the amount of sodium is 0 to 1,690 ppm; if the compound comprises a cesium sulfate, the amount of cesium is 0 to 275 ppm; if the compound comprises a sodium hydroxide, the amount of sodium is 0 to 35 ppm; if the compound is a potassium hydroxide, the amount of potassium is 0 to 50 ppm; and/or if the compound comprises a cesium hydroxide, the amount of cesium is 0 to 140 ppm.

Aspect 41. A polycarbonate composition made by a system according to any of aspects 33-40.

Aspect 42. A polycarbonate composition, the composition having an average molecular weight of between about 8 and about 70 kDalton (polystyrene basis) and exhibiting a Fries rearrangement level of less than 900 ppm by weight of the product.

Aspect 43. The polycarbonate composition of aspect 42, wherein the Fries rearrangement is between about 100 and about 900 ppm by weight of the product, e.g., between about 150 and about 850, between about 200 and about 800, between about 250 and about 750, between about 300 and about 700, between about 350 and about 650, between about 400 and about 600, between about 450 and about 550, or even about 500 ppm.

Aspect 44. The polycarbonate product of aspect 38, wherein the polycarbonate has an average molecular weight of between about 25 kDalton and about 40 kDalton (polystyrene basis).

Aspect 45. The polycarbonate composition of any of aspects 41-44, wherein the polycarbonate is made according to the method of any of aspects 1-12, 14-20 or by a system according to any of aspects 23-32 or 33-40.

Aspect 46: In any of aspects 1, 3, 9, 11, 14, 15, 19, 20, and 23, wherein the beta catalyst comprises an amount of metal and wherein the amount of metal present is based upon which compound is present, wherein the metal comprises at least one of sodium, potassium, cesium; and wherein: if the compound comprises a sodium sulfate, the amount of sodium is 0 to 1,671 ppm; if the compound comprises a cesium sulfate, the amount of cesium is 0 to 252 ppm; if the compound comprises a sodium hydroxide, the amount of sodium is 0 to 29 ppm; if the compound is a potassium hydroxide, the amount of potassium is 0 to 43 ppm; and/or if the compound comprises a Cs hydroxide, the amount of Cs is 0 to 132 ppm.

Aspect 47: The polycarbonate composition of any of aspects 41-45, wherein the polycarbonate comprises less than or equal to 33 ppb of molybdenum; less than or equal to 33 ppb of vanadium; less than or equal to 33 ppb of chromium; less than or equal to 75 ppb of titanium; less than or equal to 375 ppb of niobium; less than or equal to 33 ppb of nickel; less than or equal to 10 ppb of zirconium; less or equal to 10 ppb iron; or any combination of the foregoing.

Aspect 48: The method of any of aspects 1-12 and 14-20, wherein the polycarbonate comprises less than or equal to 33 ppb of Mo; less than or equal to 33 ppb of vanadium; less than or equal to 33 ppb of Cr; less than or equal to 75 ppb of Ti; less than or equal to 375 ppb of Nb; less than or equal to 33 ppb of Ni; less than or equal to 10 ppb of Zr; less or equal to 10 ppb Fe; or any combination of the foregoing.

Aspect 49: The system of any of aspects 23-32 and 33-40, wherein the system is configured to produce or produces a polycarbonate that comprises less than or equal to 33 ppb of molybdenum; less than or equal to 33 ppb of vanadium; less than or equal to 33 ppb of chromium; less than or equal to 75 ppb of titanium; less than or equal to 375 ppb of niobium; less than or equal to 33 ppb of nickel; less than or equal to 10 ppb of zirconium; less or equal to 10 ppb iron; or any combination of the foregoing.

In embodiments where TPPA is used, the metal content (as a wt % of the TPPA) may suitably be below about 25 ppm, below about 20 ppm, or even below about 15 ppm. In some embodiments where TPPO is used, the TPPO content (as a wt % of TPPA that may be present) may be suitably be below 2000 ppm. The organic purity level is suitably about 99.80% or greater; the term "organic purity level" refers to the wt % of the desired organic component (e.g., TPPA) as a percentage of other substances of organic nature, with the sum of the desired organic component and the other substances adding up to 100%.

Aspect 50. The method of any of aspects 1-12 and 14-20, wherein the beta catalyst comprises TPPA, and wherein the TPPA metal content is less than about 25 ppm.

Aspect 51. The method of any of aspects 1-12, 14-20, and 50, wherein the beta catalyst comprises TPPO and TPPA, and wherein the TPPO content is less than about 2000 ppm as a percentage of the TPPA.

Aspect 52. The method of any of aspects 1-12, 14-20, and 50-51, wherein the beta catalyst comprises TPPA, and wherein the organic purity level of the TPPA is about 99.80% or greater.

The terminology used herein is for the purpose of describing particular aspects only and is not intended to be limiting. As used in the specification and in the claims, the term "comprising" can include the embodiments "consisting of" and "consisting essentially of" Unless defined otherwise, all technical and scientific terms used herein have the same meaning as commonly understood by one of ordinary skill in the art to which this disclosure belongs. In this specification and in the claims which follow, reference will be made to a number of terms which shall be defined herein. As used herein, when referring to a "reactive group", e.g., having a reactive OFF group or a reactive ester group, the reactivity is with respect to polycarbonate. All ranges disclosed herein are inclusive of the endpoints, and the endpoints are independently combinable with each other (e.g., ranges of "up to 25 wt %, or, more specifically, 5 to 20 wt %", is inclusive of the endpoints and all intermediate values of the ranges of "5 to 25 wt %," etc.). "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the film(s) includes one or more films). Reference throughout the specification to "one embodiment," "another embodiment," "an embodiment," and so forth, means that a particular element (e.g., feature, structure, and/or characteristic) described in connection with the embodiment is included in at least one embodiment described herein, and may or may not be present in other embodiments. It should be understood that the described elements may be combined in any suitable manner in the various embodiments. Disclosure of a narrower range or more specific group in addition to a broader range is not a disclaimer of the broader range or larger group. While particular embodiments have been described, alternatives, modifications, variations, improvements, and substantial equivalents that are or may be presently unforeseen may arise to Applicants or others skilled in the art. Accordingly, the appended claims as filed and as they may be amended are intended to embrace all such alternatives, modifications variations, improvements, and substantial equivalents.

What is claimed:

1. A polymerization process comprising:
   melt polymerizing a carbonate and a dihydroxy compound in the presence of an amount of a beta organic catalyst so as to give rise to a polycarbonate product,
   wherein the amount of beta organic catalyst comprises at least one onium salt and also comprises triphenyl phosphonium oxide, and
   wherein the triphenyl phosphonium oxide represents less than about 0.3 weight % of the sum of the weights of the at least one onium salt and the triphenyl phosphonium oxide in the amount of beta organic catalyst.

2. The polymerization process of claim 1, wherein (a) the at least one onium salt comprises tetramethyl phosphonium acetate, tetrapropyl phosphonium acetate, tetrabutyl phosphonium acetate, or tetraphenyl phosphonium acetate (b), the triphenyl phosphonium oxide represents less than about 0.2 weight % of the sum of the weights of the at least one onium salt and triphenyl phosphonium oxide in the amount of beta organic catalyst, or (a) and (b).

3. The polymerization process of claim 1, wherein the melt polymerizing is performed in the presence of an alpha inorganic catalyst that comprises one or more alkali metal salts, one or more alkaline earth metal salts, or any combination thereof.

4. The polymerization process of claim 1, wherein the polycarbonate product is an oligomerization product having a number average molecular weight of less than or equal to about 13 kDalton (polystyrene basis) and wherein the oligomerization product exhibits a Fries rearrangement level of less than about 500 ppm.

5. The polymerization process of claim 1, wherein the polycarbonate product is a polymerization product having a number average molecular weight of more than about 13 kDalton (polystyrene basis) and wherein the polymerization product exhibits a Fries rearrangement level of from about 300 ppm to about 1200 ppm.

6. The polymerization process of claim 1, wherein the beta organic catalyst comprises an amount of metal and wherein the amount of metal present is based upon the weight of the catalyst compound is present, wherein the metal comprises at least one of sodium, potassium, cesium; and wherein: if the compound comprises a sodium sulfate, the amount of sodium is 1 ppm to 1,690 ppm; if the compound comprises a cesium sulfate, the amount of cesium is 10 ppm to 275 ppm; if the compound is a potassium hydroxide, the amount of potassium is greater than 0 to 50 ppm; and/or if the compound comprises a cesium hydroxide, the amount of cesium is 10 ppm to 140 ppm.

7. The polymerization process of claim 1, further comprising adding a quencher composition.

8. A system comprising:
a reactor chain configured to synthesize a polycarbonate product; and
an amount of beta organic catalyst,
wherein the amount of beta organic catalyst comprises at least one onium salt and also comprises triphenyl phosphonium oxide, and
wherein the triphenyl phosphonium oxide represents less than about 0.3 weight % of the sum of the weights of the at least one onium salt and the triphenyl phosphonium oxide in the amount of beta organic catalyst.

9. The system of claim 8, wherein the reactor chain comprises a first stage configured to synthesize polycarbonate oligomerization product having a number average molecular weight of less than or equal to about 13 kDalton (polystyrene basis).

10. The system of claim 8, wherein the reactor chain further comprises a second stage configured to synthesize a polycarbonate polymerization product having a number average molecular weight of more than about 13 kDalton (polystyrene basis).

11. The system of claim 8, wherein the reactor chain further comprises a second stage configured to synthesize a polycarbonate polymerization product having a number average molecular weight of from about 25,000 to 70,000 Dalton (polystyrene basis).

12. The system of claim 8, wherein the polycarbonate product is an oligomerization product having a number average molecular weight of less than or equal to about 13 kDalton (polystyrene basis) and wherein the oligomerization product exhibits a Fries rearrangement level of less than about 500 ppm.

13. The system of claim 8, wherein the system is configured to synthesize a polycarbonate polymerization product that exhibits a Fries rearrangement level of from about 300 ppm to about 1100 ppm.

14. The system of claim 8, wherein the beta organic catalyst comprises an amount of metal and wherein the amount of metal present is based upon which compound is present, wherein the metal comprises at least one of sodium, potassium, cesium; and wherein: if the compound comprises a sodium sulfate, the amount of sodium is 1 ppm to 1,690 ppm; if the compound comprises a cesium sulfate, the amount of cesium is 10 ppm to 275 ppm; if the compound is a potassium hydroxide, the amount of potassium is greater than 0 to 50 ppm; and/or if the compound comprises a cesium hydroxide, the amount of cesium is 10 ppm to 140 ppm.

15. A polycarbonate composition made via the system of claim 8, the polycarbonate composition having a number average molecular weight of between about 8 and about 70 kDalton (polystyrene basis) and exhibiting a Fries rearrangement level of less than 900 parts per million by weight of the product.

16. The polymerization process of claim 1, wherein the dihydroxy compound comprises a diaryl carbonate ester.

17. The polymerization process of claim 16, further comprising preparing the diaryl carbonate ester by transesterification reaction containing a dialkylcarbonate, phosgenation of phenol.

18. The polymerization process of claim 16, wherein the diaryl carbonate ester comprises bis(4-nitrophenyl)carbonate, bis(2-chlorophenyl)carbonate, bis(4-chlorophenyl)carbonate, bis(methyl salicyl)carbonate, bis(4-methylcarboxylphenyl)carbonate, bis(2-acetylphenyl)carboxylate, bis(4-acetylphenyl)carboxylate, or a combination comprising at least one of the foregoing.

19. The polymerization process of claim 16, wherein the diaryl carbonate ester comprises less than or equal to 23 parts per billion by weight of molybdenum; less than or equal to 23 parts per billion by weight vanadium; less than or equal to 23 parts per billion by weight chromium; less than or equal to 57 parts per billion by weight titanium; less than or equal to 284 parts per billion by weight of niobium; less than or equal to 23 parts per billion by weight of nickel; less than or equal to 6 parts per billion by weight zirconium; less than or equal to 6 parts per billion by weight of iron.

20. The polymerization process of claim 1, wherein:
the triphenyl phosphonium oxide represents less than or equal to about 0.280 weight % of the sum of the weights of the at least one onium salt and the triphenyl phosphonium oxide in the amount of beta organic catalyst and
the at least one onium salt comprises tetraphenyl phosphonium acetate.

* * * * *